US011077209B2

(12) United States Patent
Pattinson et al.

(10) Patent No.: US 11,077,209 B2
(45) Date of Patent: Aug. 3, 2021

(54) USE OF CEREBRAL NITRIC OXIDE DONORS IN THE ASSESSMENT OF THE EXTENT OF BRAIN DYSFUNCTION FOLLOWING INJURY

(71) Applicant: OXFORD UNIVERSITY INNOVATION LIMITED, Oxford (GB)

(72) Inventors: Kyle Pattinson, Oxford (GB); Jon Westbrook, Oxford (GB); Matt Rowland, Oxford (GB); Payashi Garry, Oxford (GB); Martyn Ezra, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 16/077,560

(22) PCT Filed: Feb. 17, 2017

(86) PCT No.: PCT/EP2017/053720
§ 371 (c)(1),
(2) Date: Aug. 13, 2018

(87) PCT Pub. No.: WO2017/140904
PCT Pub. Date: Aug. 24, 2017

(65) Prior Publication Data
US 2019/0030191 A1 Jan. 31, 2019

(30) Foreign Application Priority Data
Feb. 19, 2016 (GB) ..................... 1602959

(51) Int. Cl.
*A61K 49/00* (2006.01)
*A61B 5/00* (2006.01)
*A61K 33/00* (2006.01)
*A61B 5/245* (2021.01)
*A61B 5/369* (2021.01)
*A61B 5/026* (2006.01)
*A61B 5/145* (2006.01)
*A61B 6/03* (2006.01)
*A61B 5/055* (2006.01)
*A61B 5/374* (2021.01)
*A61B 5/1455* (2006.01)

(52) U.S. Cl.
CPC ........ *A61K 49/0004* (2013.01); *A61B 5/0042* (2013.01); *A61B 5/0075* (2013.01); *A61B 5/0263* (2013.01); *A61B 5/14525* (2013.01); *A61B 5/245* (2021.01); *A61B 5/369* (2021.01); *A61B 5/4064* (2013.01); *A61B 5/4848* (2013.01); *A61B 6/037* (2013.01); *A61K 33/00* (2013.01); *A61B 5/026* (2013.01); *A61B 5/055* (2013.01); *A61B 5/14542* (2013.01); *A61B 5/14553* (2013.01); *A61B 5/374* (2021.01)

(58) Field of Classification Search
CPC .. A61K 49/0004; A61K 33/00; A61B 5/0042; A61B 5/0263; A61B 5/04008; A61B 5/14525; A61B 6/037; A61B 5/0075; A61B 5/0476; A61B 5/4848; A61B 5/14553; A61B 5/4064; A61B 5/026; A61B 5/048; A61B 5/055; A61B 5/14542
See application file for complete search history.

(56) References Cited

U.S. PATENT DOCUMENTS

2015/0125553 A1   5/2015 Gladwin et al.

FOREIGN PATENT DOCUMENTS

| CA | 2899602 A1    | 8/2014  |
|----|---------------|---------|
| RU | 2140651 C1    | 10/1999 |
| WO | 9918949 A1    | 4/1999  |
| WO | 2005004884 A2 | 1/2005  |
| WO | 2009035550 A1 | 3/2009  |
| WO | 2010093746 A1 | 8/2010  |

OTHER PUBLICATIONS

Garry et al., "Electroencephalographic Response to Sodium Nitrate May Predict Delayed Cerebral Ischemia After Severe Subarachnoid Hemorrhage", Critical Care Medicine, vol. 44 No. 11, Nov. 2016, pp. e1067-e1073.
Garry et al., "The role of the nitric oxide pathway in brain injury and its treatment from bench to bedside", Experimental Neurology, vol. 263, (2015) pp. 235-243.
Classen, J. et al., "Quantitative continuous EEG for detecting delayed cerebral ischemia in patients with poor-grade subarachnoid hemorrhage", Clinical Neurophysiology, Elsevier Science, IE., vol. 115, No. 12, Aug. 3, 2004, pp. 2699-2710.
Tisdall, M., et al., "The Prognostic Value of Brain Extracellular Fluid Nitric Oxide Metabolites After Traumatic Brain Injury", Neurocrit Care, vol. 19, No. 1, Oct. 15, 2013, pp. 65-68.
International Search Report and Written Opinion from corresponding international application PCT/EP2017/053720 dated Apr. 5, 2017 (16 pages).
Search Report from IPO in corresponding GB application 1602959.7 dated Nov. 11, 2016 (5 pages).

(Continued)

*Primary Examiner* — Robert S Cabral
(74) *Attorney, Agent, or Firm* — McDermott Will & Emery LLP

(57) ABSTRACT

The invention provides a cerebral nitric oxide donor for use in a method for assessing the extent of brain dysfunction following brain injury, said method comprising contacting at least a portion of the brain of a subject with a brain injury with said cerebral nitric oxide donor and determining whether or not there is a subsequent change in one or more aspects of brain physiology, wherein the extent by which said one or more aspects of brain physiology improves is indicative of the extent of brain dysfunction.

13 Claims, 3 Drawing Sheets

(56) References Cited

OTHER PUBLICATIONS

Figure 1:
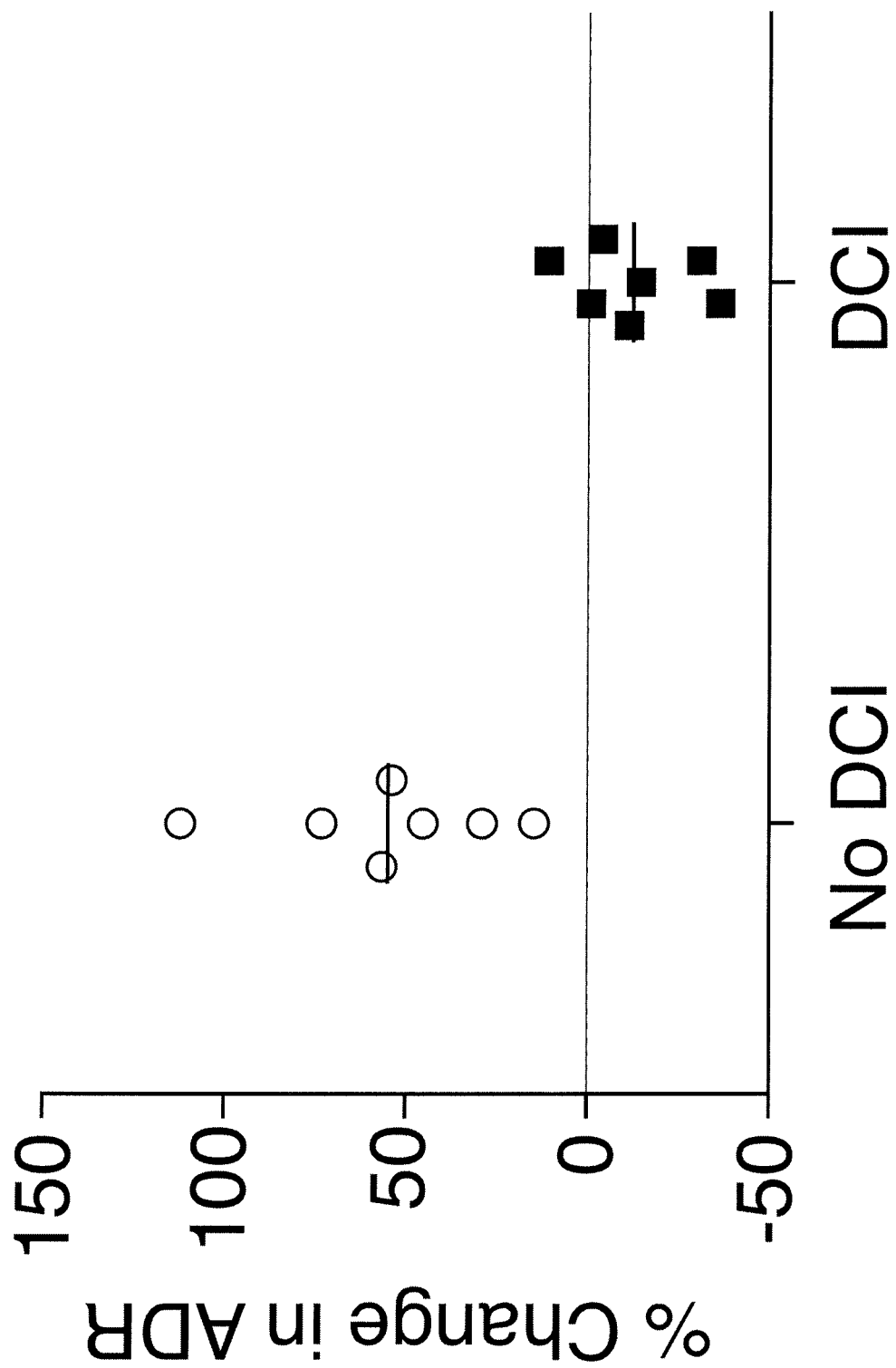

Rots, M.L., et al. "Continuous EEG Monitoring for Early Detection of Delayed Cerebral Ischemia in Subarachnoid Hemorrhage: a Pilot Study" Neurocritical Care, vol. 24, No. 2, pp. 207-216, Apr. 1, 2016.
Fathi, et al., "Reversal of cerebral vasospasm via intravenous sodium nitrite after subarachnoid hemorrhage in primates: Laboratory investigation", J Neurosurg, Dec. 2011,115(6), pp. 1213-1220.
Franca-Silva et al., "Organic Nitrates: Past, Present and Future", Molecules, 2014, pp. 15314-15323, doi:10.3390/molecules190915314.
Ignarro, et al., "Nitric Oxide Donors and Cardiovascular Agents Modulating the Bioactivity of Nitric Oxide an Overview", Jan. 11/25, 2002, Circulation Research, pp. 21-28.
Jung et al., "Early Intravenous Infusion of Sodium Nitrite Protects Brain Against In Vivo Ischemia-Reperfusion Injury", Stroke, 2006; 37:2744-2750.
Liang, et al., "Nitric oxide generating/releasing materials", Future Science OA, 2015, 1(1), FSO54.
Miller et al., "Recent developments in nitric oxide donor drugs", British Journal of Pharmacology, 2007, vol. 151, pp. 305-321.
Pluta et al., "Nitrite Infusions to Prevent Delayed Cerebral Vasospasm in a Primate Model of Subarachnoid Hemorrhage", JAMA, vol. 293, No. 12, Mar. 23/30, 2005, pp. 1477-1484.
Pluta et al.,"Increased cerebral blood flow but no reversal or prevention of vasospasm in response to L-arginine infusion after subarachnoid hemorrhage", J Neurosurg, 2000, vol. 92, pp. 121-126.
Ryszard M. Pluta, "Delayed cerebral vasospasm and nitric oxide: review, new hypothesis, and proposed treatment", Pharmacology & Therapeutics, 2005, vol. 105, pp. 23-56.
Oldfield, et al., "Safety and pharmacokinetics of sodium nitrite in patients with subarachnoid hemorrhage: a Phase IIA study", J Neurosurg , Sep. 2013, vol. 119, pp. 634-641.

USE OF CEREBRAL NITRIC OXIDE DONORS IN THE ASSESSMENT OF THE EXTENT OF BRAIN DYSFUNCTION FOLLOWING INJURY

The present invention relates to the assessment of the extent of brain dysfunction in subjects having undergone brain injury using cerebral nitric oxide (NO) donors as molecular probes. The invention is based on the surprising observation that the acute normalising response of brain activity in the injured brain to exogenous nitric oxide correlates to the outcome of the patient. More particularly, it has been found that the worse the outcome following injury the more limited are the normalising effects of exogenous nitric oxide on the function of that brain as measured by non- or minimally invasive brain monitoring techniques, e.g. quantitative electroencephalography (qEEG). The present invention therefore provides a rapid, sensitive and minimally disruptive technique to determine the extent of brain dysfunction following injury which can assist in the rapid development of tailored care plans for critically ill patients. As shown in the Examples, the present invention can effectively stratify patients with the same clinical severity scores and other currently used measures of brain dysfunction in terms of eventual outcomes (delayed cerebral ischemia and long-term physical outcome), thus giving physicians information with which they can ensure each of these patients are treated appropriately in view of the extent of their brain injury. More particularly, the present invention can be used to determine the likelihood of a secondary brain injury following a primary brain injury and/or the likely timecourse thereof, thus enabling early interventions to be made.

Currently, it is difficult to predict the evolution of acute brain injuries. During an initial event the brain may encounter a number of damaging processes depending of the mechanism of the event (e.g. contusion, axonal shearing and damage to the meninges and the blood brain barrier). Together the immediate outcome of these processes is considered a primary brain injury. In the hours and days following the primary injury the brain may undergo secondary (or indirect) injury from processes initiated by the primary injury. In these contexts, the aim of clinical care is to prevent the development of secondary injury. However, the extent and evolution of the secondary brain injury cannot easily be determined from currently available techniques. This results in difficulty guiding treatment and predicting outcome.

Currently used clinical scoring systems have poor accuracy and current bedside clinical monitoring is often subjective and difficult to interpret. Bedside monitoring modalities are used to determine the physiological function of the different components of the brain. For example electroencephalography (EEG) determines the electrophysiological action of the neurons, Near Infrared Spectroscopy (NIRS) and Transcranial Doppler (TCD) the cerebral vascular function and Cerebral Microdialysis (CMD) the cerebral metabolic function. A number of parameters derived from these monitoring modalities have been shown to correlate with the severity of brain injury. However, when used alone, bedside monitoring modalities such as EEG, NIRS, TCD and CMD typically require long recording periods (sometimes days), to give useful clinical information. Values at a single time point have little diagnostic value, meaning that multiple recordings are required to discern a trend, which is usually determined subjectively.

In contrast, instead of looking for the long-term evolution of abnormal patterns indicative of brain dysfunction in brain monitoring modalities, the present invention takes a dynamic approach and tests the injured brain's more acute physiological response to a molecular probe. Such an approach allows diagnostically useful information to be obtained in much shorter time scales, e.g. in the order of hours and minutes rather than days.

The inventors have found, surprisingly, that nitric oxide (NO) donors may be used reliably as such molecular probes in the context of the assessment of brain dysfunction following injury.

NO is a physiological signalling molecule having numerous roles in human and animal physiology. In the brain, naturally derived NO (from the action of endothelial NO synthase (eNOS)) has been shown to play an important role in protecting the brain after injury, through a number of mechanisms such as vasodilatation and attenuation of detrimental metabolic pathways. However, following brain injury the eNOS system pathway can be disrupted, with the extent of disruption correlating to the severity of injury. This disruption limits the amount of neuroprotection provided and renders the brain more susceptible to the development of secondary injury. Cerebral NO donors, e.g. sodium nitrite, used in animal models, appear to replicate the benefits of eNOS derived NO and reduce the incidence of secondary injury.

In view of such findings it could be expected that in those subjects with the worst underlying brain injury, i.e. those most likely to have poor outcome, there would be the greatest disruption of brain nitric oxide pathways and therefore in such subjects exogenous NO would elicit the strongest normalising response upon administration. Similar response patterns would be predicted upon long term use of cerebral NO donors as therapeutics.

On the contrary, the inventors have found that the brain function of those subjects who eventually had poor outcome showed little or no acute response to exogenous NO administered transiently in the form of sodium nitrite, whereas a positive acute response to transient exposure to nitrite was associated with good outcome. The timecourse of sodium nitrite exposure and associated observations on the extent of the normalising response is such that the effects observed cannot be attributed to a therapeutic effect elicited by the exogenous NO delivered by the sodium nitrite. Instead, it is believed that the short term exposure of an injured brain to exogenous NO functions as a diagnostic probe enabling the clinician to test rapidly the integrity of the NO pathways, and thus the severity of injury. The acute response of an injured brain to transient exposure to exogenous NO is therefore considered to be purely a marker of brain injury.

Thus, in a first aspect of the invention there is provided a cerebral nitric oxide donor for use in a method for assessing the extent of brain dysfunction following brain injury, said method comprising contacting at least a portion of the brain of a subject with a brain injury with said cerebral nitric oxide donor and determining whether or not there is a subsequent change in one or more aspects of brain physiology, wherein the extent by which said one or more aspects of brain physiology improves is indicative of the extent of brain dysfunction.

Expressed differently the invention provides a method for assessing the extent of brain dysfunction following brain injury in a subject, said method comprising contacting at least a portion of the brain of the subject with said cerebral nitric oxide donor and determining whether or not there is a subsequent change in one or more aspects of brain physiology, wherein the extent by which said one or more aspects of brain physiology improves is indicative of the extent of brain dysfunction.

Expressed differently again the invention provides the use of a cerebral nitric oxide donor in the manufacture of a physiologically acceptable composition for use in a method for assessing the extent of brain dysfunction following brain injury, said method comprising contacting at least a portion of the brain of a subject with a brain injury with said cerebral nitric oxide donor and determining whether or not there is a subsequent change in one or more aspects of brain physiology, wherein the extent by which said one or more aspects of brain physiology improves is indicative of the extent of brain dysfunction.

The objective of the contacting step is to expose at least a portion of the injured brain, e.g. an injured part of the injured brain, to an amount of the cerebral NO donor which is (or would be predicted to be) effective in provoking an improvement in one or more aspects of brain physiology in an injured brain capable of responding to exogenous NO, e.g. the NO donor. The extent by which the physiology of the injured brain improves following exposure to the cerebral NO donor (or the lack of improvement or worsening in brain physiology) provides an indication of the extent of the patient's brain dysfunction prior to exposure to the NO donor. More specifically, the greater the improvement in said one or more aspects of brain physiology the less the extent of dysfunction. Thus, the less the improvement the greater the extent of dysfunction and, as such, a worsening of, or a lack of change in, said one or more aspects of brain physiology is also indicative of a greater extent of dysfunction.

In these embodiments, the method may have a further step of assessing the extent of brain dysfunction following brain injury based on the foregoing steps, specifically based on whether or not, or the extent to which, said one or more aspects of brain physiology improves.

An indication of the extent of brain dysfunction in turn allows the clinician to diagnose likely long-term clinical outcome or, more simply, to diagnose the patient's brain health following injury or clinical impact of a brain injury. Following a primary brain injury, an indication of the extent of brain dysfunction allows the clinician to diagnose the likelihood of a secondary injury occurring and/or the likely timecourse thereof.

A cerebral nitric oxide donor is a physiologically acceptable substance capable of raising NO levels (including any and all redox forms) in the brain without requiring the action of a nitric oxide synthase, specifically eNOS. For convenience and brevity the term "cerebral nitric oxide donor" as used herein includes NO per se, unless context dictates otherwise.

The cerebral NO donor may a direct NO donor, i.e. a molecule which spontaneously releases NO under certain conditions, or an indirect NO donor which requires enzymatic metabolism.

Direct NO donors are typically molecules with either a nitroso or nitrosyl functional group (—NO), e.g. C-nitroso compounds, S-nitroso compounds, N-nitroso compounds, O-nitroso compounds, metal nitrosyls and halide nitrosyls, or inorganic nitrites. Specific examples include sodium nitroprusside, the p-nitrosophosphates (e.g. sodium trioxodinitrate), the diazeniumdiolates (NONOates) (e.g. diethylamine/NO, diethylenetriamine/NO, spermine NONOate, V-PYRRO/NO, PROLI/NO, JS-K), the oxatriazoliums (sydnonimines) (e.g. 3-morpholinosydnonimine) the furoxans, the S-nitrosothiols (e.g. S-nitroso-glutathione, S-nitroso-N-acetylpenicillamine, S-nitroso-N-valerylpenicillamine, S-nitroso-albumin, S-NO-N-acetyl cysteine, S-NO-diclofenac), nitrite salts and nitrite coordination complexes.

Nitrite salts of use in the invention may be formed from any physiologically acceptable cation and one or more nitrite anions. Suitable cations include but are not limited to alkali metals (e.g. lithium, sodium, potassium, rubidium, caesium, francium), alkaline earth metals (e.g. beryllium, magnesium, calcium, strontium, barium, radium), transition metals (e.g. zinc, iron, copper, nickel, cobalt, manganese), ammonium and organic cations (e.g. imidazolium, pyridinium, pyrrolidinium, phosphonium, quaternary ammonium, sulfonium). Nitrite salts of alkali metals or alkaline earth metals (e.g. lithium, sodium, potassium, magnesium, and calcium) are preferred.

Indirect NO donors include the organic nitrate and nitrite esters, e.g. nitroglycerin, amyl nitrite, isosorbide dinitrate, isosorbide 5-mononitrate, 2-[(pyridin-3-ylcarbonyl)amino] ethyl nitrate (nicorandil), and pentaerythritol tetranitrate (PETN).

In certain embodiments the cerebral NO donor is not a naturally occurring compound (e.g. NO), i.e. is artificial (man-made).

It will immediately be seen that in choosing a cerebral NO donor the skilled person must take into account delivery of the donor to the injured brain. If administration is not directly into the brain the influence of the blood brain barrier on delivery of the selected NO donor to the brain will need to be considered. If a patient's blood brain barrier is intact or substantially intact, the selected NO donor will need to be able to cross that barrier in the subject undergoing assessment. It may however be the case that the extent of a patient's brain injury is such that the blood brain barrier is compromised and so such considerations are less relevant.

It will also be apparent that it is advantageous to use an NO donor which is selective for the brain. By this it is meant that the donor preferentially (selectively) releases NO in brain tissue as compared to other tissue types. It may be still further advantageous to use an NO donor which is selective for ischemic tissues, i.e. tissues which are hypoxic and at a lower pH than normal tissues (acidosis), e.g. ischemic areas of the brain. The inorganic nitrite salts, preferably lithium, sodium, potassium, magnesium, and calcium nitrite, more preferably sodium and potassium nitrite, may have such properties.

The invention encompasses the use of a single cerebral nitric oxide donor or a mixture (multiplicity/plurality) of different cerebral nitric oxide donors. Thus, for example, a combination of different cerebral nitric oxide donors (e.g. two or more) may be used. Such agents may be administered together or separately, e.g. sequentially or simultaneously.

The term "brain injury" is used in a broad sense to refer to acute non-specific destruction of, or physical/structural damage to, a part of a brain or the structures thereof, including non-specific neuronal death. It is not intended to cover the chronic structural changes induced by neurodegenerative diseases or conditions or tumours.

The injury may be a primary injury or a secondary injury. As a primary injury, this may include the immediate results of physical trauma (external physical forces have caused the damage), stroke (i.e. acute hypoxic brain injury (lack of oxygen) has caused the damage) and/or acute haemorrhagic brain injury (bleeding within the cranial vault has caused the damage) and brain injury caused by chemical agents or a pathogenic microorganism (including a virus). Such insults cause some or all of contusion, laceration, axonal shearing and damage to the meninges and the blood brain barrier, in particular, intracerebral haemorrhage, subdural haemorrhage, subarachnoid haemorrhage, epidural haemorrhage, cerebral contusion, cerebral laceration, axonal stretch injury.

As a secondary injury this may include delayed hypoxic brain injury, delayed haemorrhagic brain injury, thrombotic brain injury, inflammatory brain injury, intracranial hypertensive brain injury, brain injury caused by cerebral oedema, brain injury caused by cerebral herniation, brain injury caused by acidosis, brain injury caused by excess free radicals, brain injury caused by hypercapnia and brain injury caused by excitotoxicity.

The term "extent of brain dysfunction" is intended to mean the extent by which the physiological functioning of the subject's brain has diverged from that of a healthy subject (or, more specifically, the function of their brain prior to their brain injury). The normal functioning of a healthy brain involves numerous physiological processes and so, in certain embodiments, the term "extent of brain dysfunction" may be considered a broad measure of brain health with the extent (or magnitude or degree) of dysfunction being a marker of likely long-term clinical (neurological) outcome for the subject, e.g. as defined by, for instance, the Modified Rankin Scale, the Glasgow Coma Score, the Extended Glasgow Outcome Score, the Barthel Scale and equivalents or modifications thereof in accepted clinical use from time to time.

In these embodiments the method in which the cerebral nitric oxide donor is used may be expressed as a method for predicting (prognosticating) long-term clinical (neurological) outcome for a subject following brain injury or diagnosing likely long-term clinical (neurological) outcome for a subject following brain injury, e.g. as defined by, for instance, the Modified Rankin Scale, the Glasgow Coma Score, the Extended Glasgow Outcome Score, the Barthel Scale, or the presence or absence of ischemia, said method comprising contacting at least a portion of the brain of the subject with said cerebral nitric oxide donor and determining whether or not there is a subsequent change in one or more aspects of brain physiology, wherein the extent by which said one or more aspects of brain physiology improves is indicative of the likely long-term clinical outcome for the subject. More specifically, the greater the improvement in said one or more aspects of brain physiology the better the outcome. In the context of the Modified Rankin Scale, a good outcome is defined as a score of 0-2, whereas a poor outcome is defined as ≥3.

In these embodiments the method may have a further step of predicting, or diagnosing likely, long-term clinical (neurological) outcome for a subject following brain injury based on the foregoing steps, specifically based on whether or not, or the extent to which, said one or more aspects of brain physiology improves, e.g. by providing a score on the Modified Rankin Scale, the Glasgow Coma Score, the Extended Glasgow Outcome Score or the Barthel Scale and equivalents or modifications thereof.

In other embodiments the extent of brain dysfunction may be assessed more specifically with focus on particular physiological processes performed by the brain, e.g. neurovascular coupling (the relationship between local neural activity and subsequent changes in cerebral blood flow), brain tissue oxygenation, cerebral blood flow, cerebral ischemia, synaptic electrical activity, and brain tissue metabolism (as defined e.g. by pH, glucose, lactate, glutamate, glutamine or N-acetylaspartate (NAA) levels). By assessing the extent of specific dysfunctions in brain physiology treatment plans can be even more precisely tailored to the particular consequences of the particular injury suffered by a patient.

The term "aspect of brain physiology" is a reference to the particular physiological processes performed by the brain that may become dysfunctional following brain injury, in particular, neurovascular coupling, brain tissue oxygenation, cerebral blood flow, cerebral ischemia, synaptic electrical activity, and brain tissue metabolism. In some instances the term may be alternatively expressed as a "measure of brain activity", which term is used in a broad sense to cover the physiological processes of the brain in general rather than the synaptic electrical activity of the brain specifically.

In accordance with the invention the one or more aspects of brain physiology targeted for analysis will include or be an aspect of brain physiology which has become dysfunctional following the brain injury.

The technique used to monitor the one or more aspects of brain physiology in accordance with the present invention is not limited and thus may include any non-invasive, minimally invasive or invasive technique, e.g. EEG (including quantitative EEG (qEEG)), magnetoencephalography (MEG), NIRS (including fNIRS), acoustocerebrography (including TCD), cerebral microdialysis (CMD), magnetic resonance imaging (MRI) (including, but not limited to, Diffusion Weighted Imaging (DWI), functional MRI (fMRI), Magnetic resonance spectroscopy (MRS), Arterial Spin Labelling (ASL)), positron emission tomography (PET), single-photon emission computed tomography (SPECT) and event-related optical signal (EROS). Bedside monitoring modalities, e.g. EEG, NIRS, TCD, CMD and EROS may be conveniently used. EEG, especially qEEG, is preferred.

In embodiments of the invention in which a generalised assessment of brain dysfunction is required, any aspect of brain physiology and any suitable technique for monitoring the same may be used. In embodiments in which a brain dysfunction is to be assessed more specifically with focus on particular physiological processes performed by the brain, the measure of brain activity to be monitored may need to be selected so as to give relevant information. The skilled person would be aware of which monitoring techniques are suited to the assessment of which brain processes For instance, synaptic electrical activity of the brain can conveniently be monitored using EEG, MEG and EROS; brain tissue metabolism and ischemia can conveniently be monitored with CMD, PET, SPECT and MRS; neurovascular coupling and brain tissue oxygenation can conveniently be monitored with NIRS and fMRI; and cerebral blood flow can conveniently be monitored with TCD and ASL.

Nevertheless, all these brain processes are not independent and will influence each other indirectly; therefore one modality does not necessarily represent a measure of a single physiological function in isolation. For example, ischemia will influence the recording of EEG and MEG. Thus, despite their basis in the electrical activity of the brain, EEG and MEG can be used to monitor a number of other physiological functions e.g. by monitoring the alpha/delta ratio and/or the relative alpha power variability as a marker of ischemia, neurovascular coupling, brain tissue oxygenation and cerebral blood flow.

Therefore changes in one aspect of the physiology of an injured brain when in contact with a nitric oxide donor have the potential to manifest as changes in others. As such, it may be that in the practice of the invention any modality that can measure changes in an aspect of brain physiology will have the capacity to determine the level of normalising response to a nitric oxide donor in any other aspect of brain physiology.

In view of the foregoing and by way of example, in certain embodiments the invention provides a cerebral nitric oxide donor for use in a method for assessing the extent of dysfunction in synaptic electrical activity following brain injury, said method comprising contacting at least a portion of the brain of a subject with said brain injury with said cerebral nitric oxide donor and determining whether or not there is a subsequent change in an EEG parameter (i.e. a measurement of synaptic electrical activity), wherein the extent by which said EEG parameter improves is indicative of the extent of dysfunction in synaptic electrical activity. More specifically, the greater the improvement in said EEG parameter the less the extent of dysfunction.

In these embodiments the method may have a further step of predicting, or diagnosing the extent of dysfunction in synaptic electrical activity based on the foregoing steps, specifically based on whether or not, or the extent to which, said EEG parameter improves.

The specific combinations of brain monitoring techniques and their associated brain processes described above may be applied mutatis mutandis to the above described embodiment. In particular, in certain embodiments the invention provides a cerebral nitric oxide donor for use in a method for assessing/diagnosing the extent of dysfunctional neurovascular coupling, disturbed neuronal activity, cerebral ischemia and/or reduced cerebral blood flow, preferably dysfunctional neurovascular coupling, following brain injury, said method comprising contacting at least a portion of the brain of a subject with said brain injury with said cerebral nitric oxide donor and determining whether or not there is a subsequent change in an qEEG parameter (e.g. the alpha/delta ratio and/or the relative alpha power variability and/or the relative delta power variability), an fNIRS parameter or an fMRI parameter, wherein the extent by which said parameter improves is indicative of the extent of dysfunctional neurovascular coupling, disturbed neuronal activity, cerebral ischemia and/or reduced cerebral blood flow. More specifically, the greater the improvement in the selected parameter the less the extent of dysfunction.

In these embodiments the method may have a further step of assessing/diagnosing the extent of dysfunctional neurovascular coupling, disturbed neuronal activity, cerebral ischemia and/or reduced cerebral blood flow based on the foregoing steps, specifically based on whether or not, or the extent to which, said qEEG, fNIRS or fMRI parameter improves.

In still further embodiments the invention provides a cerebral nitric oxide donor for use in a method for assessing/diagnosing the extent of, or risk of developing, delayed cerebral ischemia following subarachnoid haemorrhage said method comprising contacting at least a portion of the brain of a subarachnoid haemorrhage subject with said cerebral nitric oxide donor and determining whether or not there is a subsequent change in an qEEG parameter (e.g. the alpha/delta ratio and/or the relative alpha power variability and/or the relative delta power variability), wherein the extent by which said qEEG parameter improves is indicative of the extent of, or risk of developing, delayed cerebral ischemia.

In these embodiments the method may have a further step of assessing/diagnosing the extent of, or risk of developing, delayed cerebral ischemia based on the foregoing steps, specifically based on whether or not, or the extent to which, said qEEG parameter improves.

In certain embodiments multiple techniques for monitoring said one or more aspects of brain physiology may underlie the assessment of general brain dysfunction or dysfunction in the same or different aspects of brain physiology.

An "improvement" in an aspect of brain physiology is a reference to a normalising change in that aspect of brain physiology, i.e. a change which takes the functioning of that physiological process towards that of an essentially healthy uninjured brain (more specifically the functioning of that physiological process towards that of the subject's brain prior to the injury). As mentioned above, in accordance with the invention the one or more aspects of brain physiology targeted for analysis will include or be an aspect of brain physiology which has become dysfunctional following the brain injury. As such, the extent by which the (dysfunctional) aspect of brain physiology improves upon exposure of the injured brain to the cerebral NO donor is negatively correlated with the extent of brain dysfunction prior to exposure to the cerebral NO donor, i.e. the greater the improvement observed in the (dysfunctional) aspect of brain physiology following contact of the injured brain with the cerebral NO donor the less brain dysfunction was present prior to contact. This may be alternatively be expressed as the more complete the normalisation of an aspect of brain physiology following contact of the injured brain with the cerebral NO donor the less brain dysfunction was present prior to contact.

In the context of the invention any detectable "improvement"/"normalisation" is therefore the acute improvement/normalisation resulting from contact of the injured brain with the cerebral NO donor, i.e. that which may be observed within 360 mins, e.g. within 300, 240, 180, 120, 90, 75, 60, 45, 30, 15, 5 or 1 mins of contact of the injured brain with the cerebral NO donor. Any improvement/normalisation may be, typically will be, transient, i.e. lasting no more than 24 hrs, e.g. no more than 18 hrs, 12 hours, 10 hrs, 8 hrs, 6 hrs, 5 hrs, 4 hrs, 3 hrs, 2 hrs, 1 hrs or 30 mins after contact of the injured brain with an effective amount of the cerebral NO donor (or the cessation of the administration of the cerebral NO donor). Consistent with this, the "dysfunction" being assessed by the methods of invention is that of the injured brain prior to contact with the cerebral NO donor. In some embodiments, the dysfunction being assessed by the methods of invention is also that following any transient normalising effects that may arise from the exposure to the NO donor.

The step of assessing the extent of brain dysfunction following brain injury based on the extent of the improvement/normalisation may be done in any convenient way capable of providing suitably accurate and reliable results. The assessment may provide qualitative, quantitative or semi-quantitative results. It may be advantageous to compare the extent of improvement/normalisation in a test subject with the results of subject(s) to which the methods of the invention have been applied previously and the outcomes for which are known. These may be described as a standard or standards. The standard to which results from a test subject are compared may be a combination of the individual results of many standard subjects. In other embodiments the clinician may make the assessment without making direct or formal comparison to standards and instead the clinician may rely on personal experience for comparison. In embodiments in which the aspect of brain function worsens or do not improve in to a significant extent, the above described comparisons are not necessary but may be done if required.

In further embodiments the method in which the cerebral nitric oxide donor is used may be focused on the assessment of brain dysfunction following a primary brain injury as a means to predict or prognosticate, or to determine, assess or diagnose the likelihood of, a secondary brain injury and/or the likely timecourse thereof. Thus, the method may be described as a method for assessing the risk of a secondary brain injury and/or the likely timecourse thereof in a subject following a primary brain injury, said method comprising contacting at least a portion of the brain of the subject with said cerebral nitric oxide donor and determining whether or not there is a subsequent change in one or more aspects of brain physiology, wherein the extent by which said one or more aspects of brain physiology improves is indicative of the risk of a secondary brain injury and/or the likely timecourse thereof. More specifically, the greater the improvement in said one or more aspects of brain physiology the less the risk of a secondary brain injury and/or the risk of an injury occurring in a shorter timecourse.

In these embodiments the method may have a further step of assessing, or diagnosing, the risk of a secondary brain injury and/or the likely timecourse thereof in a subject following a primary brain injury based on the foregoing steps, specifically based on whether or not, or the extent to which, said one or more aspects of brain physiology improves.

"Assessing the risk of a secondary brain injury" refers to the determination of the chance or the likelihood that the subject will develop a secondary brain injury. This may be expressed as a numerical probability in some embodiments. The risk decreases the greater the extent by which said measure of brain activity improves. The above definition of "improvement" applies to these embodiments of the invention and should be construed accordingly. The likely timecourse of secondary brain injury refers to the temporal dimensions to the secondary brain injury and its onset. As such, the invention can provide the clinician with an indication of how soon a secondary brain injury will manifest as well as being able to provide an indication of the risk that the event will occur per se. Thus, the invention can provide an indication of the likelihood of secondary brain injury occurring within a certain time period.

In certain embodiments specific secondary brain injuries may be the focus of this embodiment of the invention, e.g. one or more of hypoxic brain injury, delayed haemorrhagic brain injury, inflammatory brain injury, intracranial hypertensive brain injury, brain injury caused by cerebral oedema, brain injury caused by cerebral herniation, brain injury caused by acidosis, brain injury caused by excess free radicals, brain injury caused by hypercapnia and brain injury caused by excitotoxicity. The one or more aspects of brain physiology and the technique with which that aspect is monitored may need to be selected accordingly as described above.

In the methods in which the cerebral nitric oxide donor is used in accordance with the invention there will typically be a step of monitoring the chosen aspect of brain physiology with the chosen monitoring technique prior to or concurrently with the contacting of the injured brain with the cerebral nitric oxide donor. This may be a qualitative, quantitative or semi-quantitative measurement. In certain embodiments such step will commence no more than 360 mins, e.g. no more than 300, 240, 180, 120, 90, 75, 60, 45, 30, 15, 5 or 1 mins prior to contact of the brain with the cerebral nitric oxide donor. Multiple measurements may be made in this period, e.g. at least every 10 mins, e.g. every, 5, 2, 1 or 0.5 minutes. In these embodiments the multiple measurements may be combined to form an average (e.g. mean) or baseline measurement. In this context the aspect of brain physiology may be monitored by means of a single parameter or multiple parameters or an algorithmically processed form of such parameter(s).

The extent by which said aspect of brain physiology improves is thereby determined in accordance with the invention in a step of monitoring the chosen aspect of brain physiology with the chosen monitoring technique after and/or concurrently with the contacting of the injured brain with the cerebral NO donor and, optionally, comparing the results of that latter monitoring phase with the results of the monitoring phase performed prior to or concurrently with the contacting of the injured brain with the cerebral NO donor. In certain embodiments the latter monitoring step will commence within 360 mins, e.g. within 300, 240, 180, 120, 90, 75, 60, 45, 30, 15, 5 or 1 mins of contact (e.g. first contact) of the brain with the cerebral NO donor. Multiple measurements may be made, e.g. at least every 10 mins, e.g. every, 5, 2, 1 or 0.5 minutes. In these embodiments the multiple measurements may be combined to form an average (e.g. mean) measurement or a continuous monitoring trace, which may or may not be continuous with the monitoring phase prior to contact with the NO donor. In further embodiments such a measurement step will be completed by no more than 24 hrs, e.g. no more than 18 hrs, 12 hours, 10 hrs, 8 hrs, 6 hrs, 5 hrs, 4 hrs, 3 hrs, 2 hrs, 1 hrs or 30 mins after contact (e.g. first contact) of the brain with an effective amount of the cerebral NO donor (or the cessation of the administration of the cerebral NO donor). In these contexts the measure of brain activity may be monitored by means of a single parameter or multiple parameters or an algorithmically processed form of such parameter(s).

In some embodiments the cerebral NO donor is contacted with the injured brain multiple times and after the final contact with an effective amount of cerebral NO donor the one or more aspects of brain physiology is monitored. In other embodiments the cerebral NO donor is contacted with the injured brain (administered to the subject) multiple times and after each (or a selection of) said contact (administration) the one or more aspects of brain physiology is monitored.

In certain embodiments the one or more aspects of brain physiology is monitored essentially continuously before, concomitantly with and, optionally, after the contacting event(s), e.g. within the above defined time periods, and the resulting monitoring trace is used to analyse the one or more aspects of brain physiology before, concomitantly with and, optionally, after the contacting/administration event (or events).

It will be clear to the skilled person that references to a contact or a contacting event include administration of the cerebral NO donor to the subject.

The methods of the invention may therefore be described as comprising:
  (i) contacting at least a portion of the brain of a subject with a brain injury with said cerebral nitric oxide donor,
  (ii) monitoring one or more aspects of brain physiology concurrently with and/or after the contacting of the injured brain with the cerebral NO donor, and
  (iii) determining whether or not there is a change in said one or more aspects of brain physiology,
  wherein the extent by which said one or more aspects of brain physiology improves is indicative of the extent of brain dysfunction.

In further embodiments the methods of the invention may therefore be described as comprising:
  (i) monitoring one or more aspects of brain physiology,
  (ii) contacting at least a portion of the brain of a subject with a brain injury with said cerebral nitric oxide donor, (iii) monitoring said one or more aspects of brain physiology concurrently with and/or after the contacting of the injured brain with the cerebral NO donor, and (iv) determining whether or not there is a change in said one or more aspects of brain physiology subsequent to said contact, wherein the extent by which said one or more aspects of brain physiology improves is indicative of the extent of brain dysfunction.

The other aspects and embodiments of the invention described herein may be expressed in this way and all features of such aspects and embodiments apply mutatis mutandis.

In view of these preferred timings it will be appreciated by the skilled person that the invention may be viewed alternatively as providing the means to accelerate methods for (i) the assessment of brain dysfunction following brain injury, (ii) the prediction or prognostication of clinical outcome following brain injury, or (iii) assessing the risk of a secondary brain injury and/or the likely timecourse thereof in a subject following a primary brain injury, in which one or more aspects of brain physiology is monitored, or to shorten the time period during which such monitoring must be undertaken in such methods.

Thus, in these embodiments the invention may be seen to provide a cerebral nitric oxide donor for use to accelerate (i) a method for assessing the extent of brain dysfunction following brain injury, or (ii) a method for the prediction or prognostication of long-term clinical outcome following brain injury, or (iii) a method for assessing the risk of a secondary brain injury and/or the likely timecourse thereof following a primary brain injury, in which method one or more aspects of brain physiology is monitored, said method comprising contacting at least a portion of the brain of a subject with a brain injury with said cerebral nitric oxide donor and determining whether or not there is a subsequent change in said one or more aspects of brain physiology wherein the extent by which said one or more aspects of brain physiology improves is indicative of the extent of brain dysfunction following brain injury, long-term clinical outcome following brain injury, and risk of a secondary brain injury and/or the likely timecourse thereof following a primary brain injury.

In further aspects, the methods in which the cerebral NO donor may be used in accordance with the invention can be considered to be methods of obtaining information relevant to the assessment of brain dysfunction, or for predicting likely clinical outcome for a subject following brain injury, or for assessing the risk of a secondary brain injury and/or the likely timecourse thereof in a subject following a primary brain injury. The methods described herein may be used alone as an alternative to other investigative techniques or in addition to such techniques in order to provide information relevant to the assessment of brain dysfunction, or for predicting likely clinical outcome for a subject following brain injury, or for assessing the risk of a secondary brain injury.

In a further aspect the methods described above may comprise a further step of therapeutically treating said subject in a manner consistent with the assessment, diagnosis, prediction, prognosis made in order to alleviate, reduce, remedy or modify at least one symptom or characteristic of the brain injury/dysfunction following injury (including the more specifically defined embodiments thereof) or to improve, mitigate, alleviate, reduce, remedy or modify the predicted clinical outcome or to accommodate the predicted clinical outcome, e.g. by providing palliative care. Such treatments may include administering a pharmaceutical composition and/or performing a surgical procedure appropriate to treat the brain injury/dysfunction following injury and/or alter or accommodate the predicted clinical outcome and/or adjusting the lifestyle of the subject in a manner appropriate to treat the brain injury/dysfunction following injury and/or alter or accommodate the predicted clinical outcome. In this regard, the invention can be considered to relate to methods for the therapeutic treatment of brain injury/dysfunction following injury (including combating the onset of secondary brain injury following a primary injury) and for guiding and/or optimising such treatments.

The subject may be any human or non-human animal subject, but more particularly may be a human or a non-human vertebrate, e.g. a non-human mammal, bird, amphibian, fish or reptile. In a preferred embodiment the subject is a mammalian subject. Veterinary uses of the invention are thus covered. The subject may be viewed as a patient. Preferably the subject is a human.

A "normal" or "healthy" subject is a subject that is considered not to have a brain injury as defined herein. Preferably such subjects will be free of any form of cerebral or neurological ailment that can cause brain dysfunction. A "normal" or "healthy" brain is a brain from the foregoing subjects. In other embodiments a normal or healthy subject will be essentially free of serious illness or disease or other medical conditions, or at least is a subject that does not have observable or detectable symptoms of any recognised serious illness or disease. In other embodiments a normal or healthy subject will be free of all illness or disease or other medical conditions, or at least does not have observable or detectable symptoms of any recognised illness or disease.

Contact between the cerebral NO donor of use in the invention and the injured brain, e.g. the injured part of the injured brain, is achieved by administering an effective amount of said cerebral NO donor to the patient taking account of appropriate parameters, e.g. the route of administration, the pharmacokinetic properties of the donor, permeability of the blood-brain barrier to the donor, the mechanism of NO release, and the age and size of the subject. An effective amount is that which would be predicted exert an improvement (normalising response) in one or more aspects of brain physiology in an injured brain capable of responding to exogenous NO. In practice, dose escalation may be required for an individual subject if initial doses show no effect.

In certain embodiments the cerebral NO donor is administered over a period of time rather than as a single bolus. This may be as a steady infusion of a liquid formulation or repeated bolus administrations. Such a treatment period may be 1 to 360 mins, e.g. 1 to 330 mins, 1 to 300 mins, 1 to 280 mins, 1 to 260 mins, 1 to 240 mins, 1 to 220 mins, 1 to 200 mins, 1 to 180 mins, 1 to 160 mins, 1 to 140 mins, 1 to 120 mins, 1 to 100 mins, 1 to 90 mins, 1 to 80 mins, 1 to 70 mins, 1 to 60 mins, 1 to 50 mins, 1 to 40 mins, 1 to 30 mins, 1 to 20 mins, 10 to 360 mins, 10 to 330 mins, 10 to 300 mins, 10 to 280 mins, 10 to 260 mins, 10 to 240 mins, 10 to 220 mins, 10 to 200 mins, 10 to 180 mins, 10 to 160 mins, 10 to 140 mins, 10 to 120 mins, 10 to 100 mins, 10 to 90 mins, 10 to 80 mins, 10 to 70 mins, 10 to 60 mins, 10 to 50 mins, 10 to 40 mins, 10 to 30 mins, 10 to 20 mins, 20 to 360 mins, 30 to 360 mins, 40 to 360 mins, 50 to 360 mins, 60 to 360 mins, 70 to 360 mins, 80 to 360 mins, 90 to 360 mins, 100 to 360 mins, 120 to 360 mins, 140 to 360 mins, 160 to 360 mins, 180 to 360 mins, 200 to 360 mins, 220 to 360 mins, 240 to 360 mins, 260 to 360 mins, 280 to 360 mins, 300 to 360 mins, 330 to 360 mins, 330 to 360 mins, 10 to 180 mins, 20 to 180 mins, 30 to 180 mins, 40 to 180 mins, 50 to 180 mins, 60 to 180 mins, 70 to 180 mins, 80 to 180 mins, 90 to 180 mins, 100 to 180 mins, 120 to 180 mins, 140 to 180 mins or 160 to 180 mins. Any ranges which may be formed from a combination of the range endpoints recited above are expressly contemplated.

The cerebral NO donors of the invention may be administered to the subject in any convenient form or by any convenient means in order to achieve effective amounts of the cerebral NO donors (and by extension NO) in the injured parts of the brain. This may include surgical or non-surgical or invasive, minimally invasive or non-invasive routes, e.g. parenteral routes (e.g. intravenous, intra-arterial, intracranial, intracerebral, intrathecal), enteral routes (e.g. oral, buccal, sublingual, rectal), or by inhalation (nebulised or gaseous form). Preferably the cerebral NO donors of use in the invention will be administered by parenteral routes, e.g. intravenous, intracranial or intracerebral).

The skilled man will be able to formulate the cerebral NO donors of use in the invention into physiologically acceptable compositions (e.g. pharmaceutical compositions or medicaments) that are adapted for these routes of administration according to any of the conventional methods known in the art and widely described in the literature.

More specifically, the cerebral NO donors of use in the invention may be incorporated, optionally together with other active agents, with one or more conventional carriers, diluents and/or excipients, to produce conventional galenic preparations such as tablets, pills, granules (including enteric coated granules), powders (e.g. inhalable powders, including dry inhalable powders), lozenges, sachets, cachets, elixirs, suspensions, emulsions, solutions, syrups, aerosols (as a solid or in a liquid medium), sprays (e.g. nasal sprays), compositions for use in nebulisers, soft and hard gelatine capsules, suppositories, sterile injectable solutions, sterile packaged powders, and the like. Enteric coated solid or liquid compositions, e.g. enteric coated tablets and enteric coated granules (which may be provided in an enteric-coated capsule or in a non-enteric-coated capsule i.e. in which the coating may or may not be an enteric coating), sterile inhalable and sterile injectable compositions are all of particular note.

Examples of suitable carriers, excipients, and diluents are lactose, dextrose, sucrose, sorbitol, mannitol, starches, gum acacia, calcium phosphate, inert alginate polymers, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Excipients and diluents of note for use in cerebral NO donor containing formulations are sterile water and sterile saline.

The compositions may additionally include lubricating agents, wetting agents, emulsifying agents, suspending agents, preserving agents, sweetening agents, flavouring agents, buffering agents, and the like.

Parenterally administrable forms, e.g. solutions suitable for delivery via intravenous, intra-arterial, intracranial, intrathecal or intracerebral routes mentioned above, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as sterile water for injection, Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975)), which is explicitly incorporated by reference herein in its entirety. The solutions can contain preservatives, antimicrobial agents, buffers and antioxidants conventionally used for parenteral solutions, excipients and other additives which are compatible with the cerebral NO donors and which will not interfere with the manufacture, storage or use of products.

Simple sterile solutions of cerebral NO donors or simple sterile liquid compositions comprising cerebral NO donors may be especially convenient for use during surgical procedures, for intravenous, intra-arterial, intracranial, intrathecal or intracerebral use and for delivery to the lungs, e.g. by nebuliser. Such formulations may consist of sterile water and the cerebral NO donor.

In other embodiments the cerebral NO donor may be provided in lyophilised form without or without additional excipients ready for dissolution in a suitable liquid vehicle immediately prior to administration.

The relative content of the cerebral NO donor in the compositions of the invention can vary depending on the dosage required, dosage form to be used and the dosage regime being followed but will be sufficient to achieve an effective amount at the target treatment area, taking account of variables such as the route of administration, the pharmacokinetic properties of the donor, permeability of the blood-brain barrier to the donor, the mechanism of NO release, and the age and size of the subject. The skilled person would know that the amounts of the cerebral NO donors can be reduced if a multiple dosing regime is followed or administration times are lengthened, or increased to minimise the number of administrations or applications or the duration of administration.

By way of example, sodium nitrite may be administered as total dose of 0.01 to 100 mg/kg, e.g. 0.05 to 100 mg/kg, 0.1 to 100 mg/kg, 0.5 to 100 mg/kg, 1 to 100 mg/kg, 5 to 100 mg/kg, 10 to 100 mg/kg, 20 to 100 mg/kg, 30 to 100 mg/kg, 40 to 100 mg/kg, 50 to 100 mg/kg, 60 to 100 mg/kg, 70 to 100 mg/kg, 80 to 100 mg/kg, 90 to 100 mg/kg, 0.01 to 50 mg/kg, e.g. 0.05 to 50 mg/kg, 0.1 to 50 mg/kg, 0.5 to 50 mg/kg, 1 to 50 mg/kg, 5 to 50 mg/kg, 10 to 50 mg/kg, 20 to 50 mg/kg, 30 to 50 mg/kg, 40 to 50 mg/kg, 0.01 to 10 mg/kg, 0.05 to 10 mg/kg, 0.1 to 10 mg/kg, 0.5 to 10 mg/kg, 1 to 10 mg/kg, 2 to 10 mg/kg, 5 to 10 mg/kg, 8 to 10 mg/kg, 0.01 to 8 mg/kg, 0.01 to 5 mg/kg, 0.01 to 2 mg/kg, 0.01 to 1 mg/kg, 0.01 to 0.5 mg/kg, 0.01 to 0.1 mg/kg, 0.01 to 0.05 mg/kg. Any ranges which may be formed from a combination of the range endpoints recited above are expressly contemplated.

The duration over which the above total doses are given may vary and as such the concentration of NO donor may be adjusted accordingly. Those regimens in which the cerebral NO donor is administered over a longer period of time may utilise a lower concentration. By way of example an intravenous infusion of sodium nitrite may be administered at a dose of 5-20 µg/kg/min for 1-360 mins, 10-50 µg/kg/min for 1-180 mins or 1-10 µg/kg/min for 180-540 mins. By way of specific illustration an intravenous infusion of sodium nitrite may be administered at a dose of 10 µg/kg/min for 60 mins, i.e. total dose of 0.6 mg/kg.

A representative aqueous solution ready for administration via intravenous, intra-arterial, intracranial intrathecal or intracerebral routes will be sterile and may contain 0.1 to 5%, e.g. 0.1 to 4%, 0.1 to 3%, 0.1 to 2%, 0.1 to 1%, 0.1 to 0.8%, 0.1 to 0.5%, 0.1 to 0.2%, 0.2 to 5%, 0.2 to 4%, 0.2 to 3%, 0.2 to 2%, 0.2 to 1%, 0.2 to 0.8%, 0.2 to 0.5%, 0.5 to 5%, 0.5 to 4%, 0.5 to 3%, 0.5 to 2%, 0.5 to 1%, 0.5 to 0.8%, 0.8 to 5%, 0.8 to 4%, 0.8 to 3%, 0.8 to 2%, 0.8 to 1%, 1 to 5%, 1 to 4%, 1 to 3%, 1 to 2%, 2 to 5%, 2 to 4%, 2 to 3%, 3 to 5%, 3 to 4%, 4 to 5%, w/v of the cerebral NO donor, the remainder being comprised of water and pharmaceutically acceptable excipients and/or other active agents if being used. Any ranges which may be formed from a combination of the range endpoints recited above are expressly contemplated. More concentrated forms may be provided ready for dilution prior to administration.

A representative tablet to be used to administer a cerebral NO donor of the invention to injured brain may contain up to 50%, e.g. up to 45%, 40%, 35% or 30% e.g. 5 to 50%, e.g. 5 to 45%, 5 to 40%, 5 to 35%, 5 to 30%, 5 to 25%, 5 to 20%, 5 to 15%, 5 to 10%, 10 to 50%, 10 to 45%, 10 to 40%, 10 to 35%, 10 to 30%, 10 to 25%, 10 to 20%, 10 to 15%, 15 to 50%, 15 to 45%, 15 to 40%, 15 to 35%, 15 to 30%, 15 to 25%, 15 to 20%, 20 to 50%, 20 to 45%, 10 to 40%, 20 to 35%, 20 to 30%, 20 to 25%, 25 to 50%, 25 to 45%, 25 to 40%, 25 to 35%, 25 to 30%, 30 to 50%, 30 to 45%, 30 to 40%, 35 to 50%, 35 to 45%, 35 to 40%, 40 to 50%, 40 to 45%, or 45 to 50% w/v or w/w of the cerebral NO donors, the remainder being comprised of pharmaceutically acceptable excipients and/or other active agents if being used. Any ranges which may be formed from a combination of the range endpoints recited above are expressly contemplated.

The invention will be further described with reference to the following non-limiting Example in which:

FIG. 1 shows percentage change in alpha/delta ratio (ADR) for each patient following administration of sodium nitrite, grouped by the later presence or absence of DCI. It can be seen that the ADR increases overall for the patients that did not develop DCI, and there is a decrease in the ADR of patients that went on to develop DCI.

Figure 2:
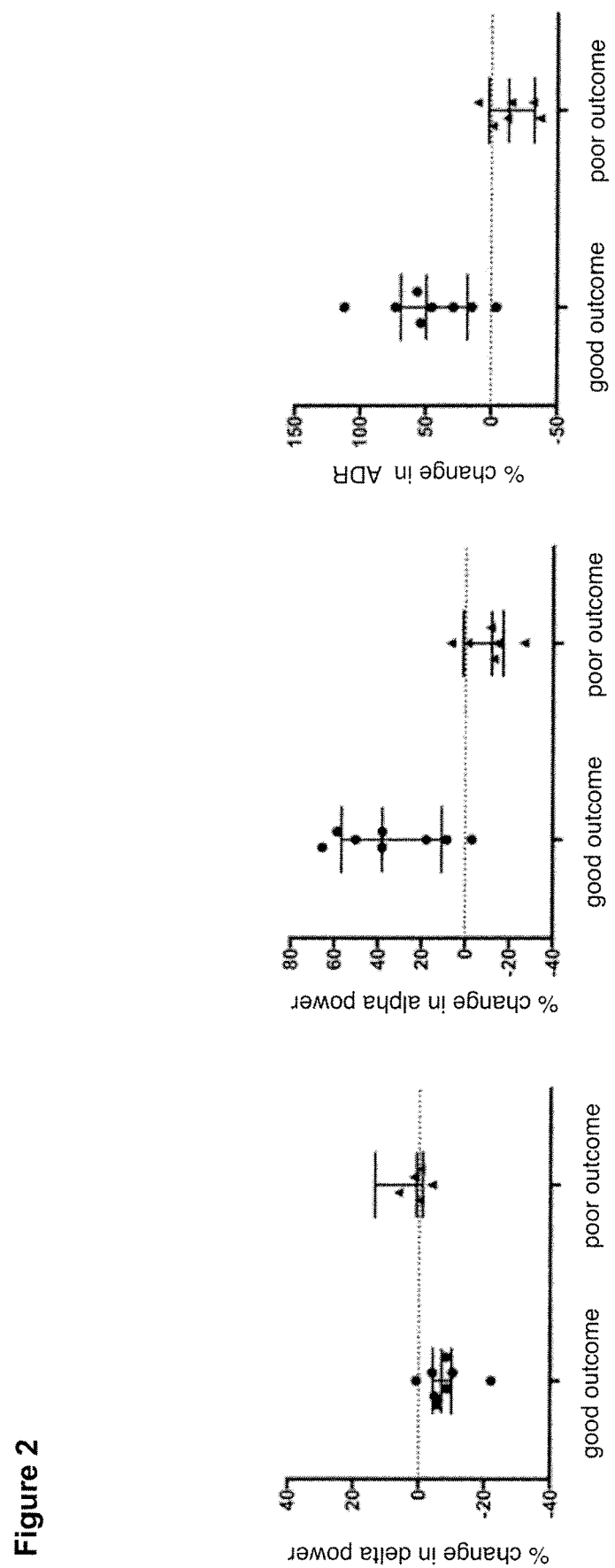
Figure 3:
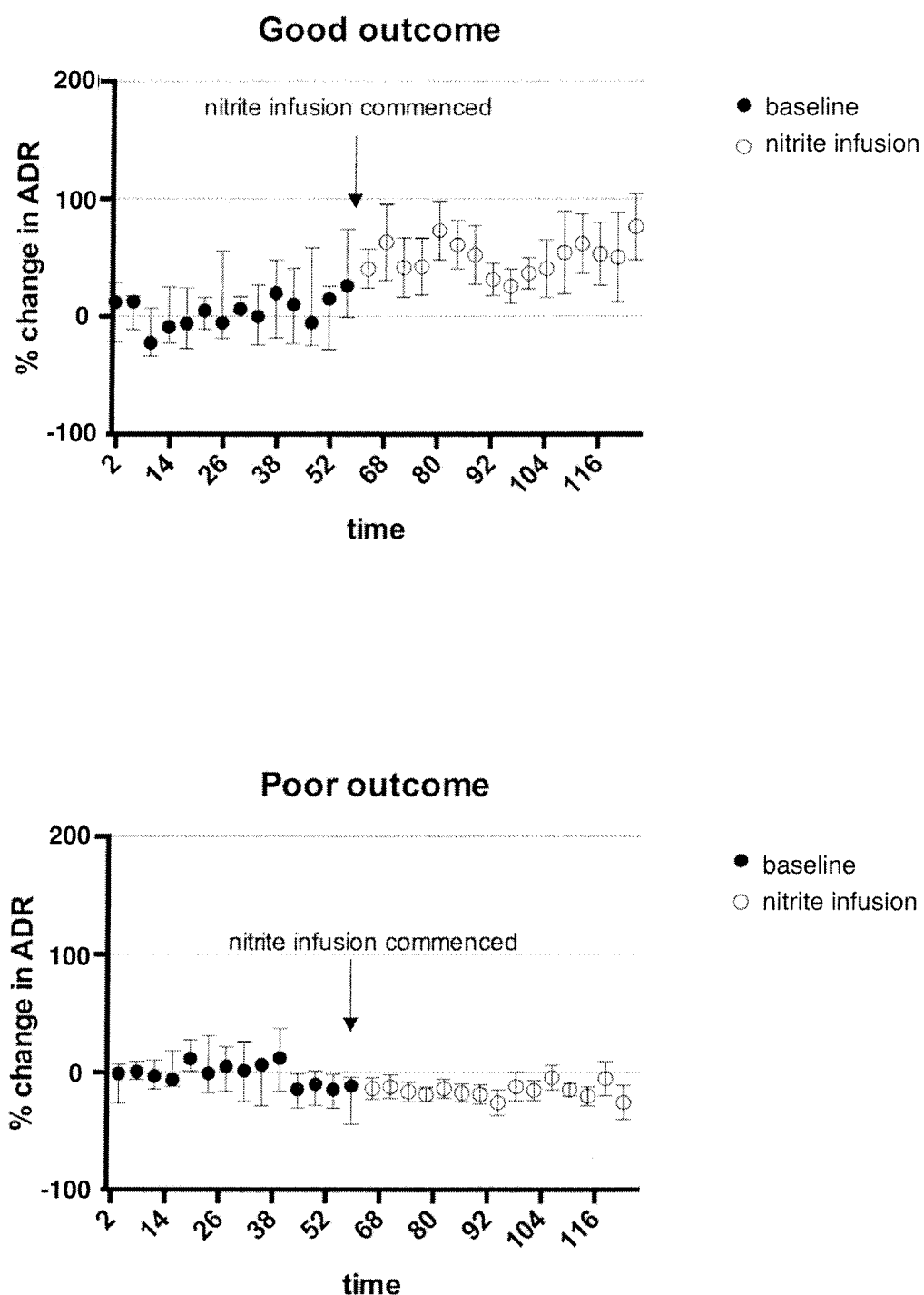

FIG. 2 shows percentage change in delta power, alpha power and alpha/delta ratio (ADR) for each patient following administration of sodium nitrite, grouped by good outcome or poor outcome. It can be seen that the alpha power and the ADR increases and the delta power decreases overall for the patients that had a good outcome. On the other hand there was no significant differences in these parameters in the poor outcome group FIG. 3 shows mean percentage change from baseline ADR over time (mins) for A: the patients with a good outcome; and B patients with a poor outcome. Circles represent the mean values at each time point, and error bars represent the standard error of the mean. The ADR increases after commencement of the nitrite infusion in the good outcome group, and does not change in the poor outcome group. The baseline over the initial 60 minutes remains stable. There is greater variability in the response to nitrite in the good outcome group, suggesting a spectrum in the response to increasing cerebral NO levels.

EXAMPLES

Example 1

EEG Response to Sodium Nitrite Predicts Delayed Ischaemia and Long-Term Clinical Outcome After Severe Subarachnoid Haemorrhage Introduction Subarachnoid haemorrhage (SAH) is usually caused by rupture of a cerebral aneurysm located in the circle of Willis. It disproportionately affects a younger population, with half of patients being under 55 years. It is often fatal, which means that the loss of productive life years approaches that of ischaemic stroke or intracerebral haemorrhage.

The main complications after SAH include early brain injury (EBI), which describes the immediate injury after SAH and occurs in the first 72 hours, and delayed cerebral ischaemia (DCI), which can occur in about 30% of patients unpredictably 3-14 days post primary haemorrhage. Much of the focus of SAH research to date has been to investigate DCI. This is because DCI remains the most important cause of morbidity and mortality in patients that survive initial aneurysm rupture and treatment.

The idea of extravasated blood from aneurysmal rupture leading to cerebral artery vasoconstriction and tissue infarction has been widely held. However, the temporal relationship between angiographic evidence of vessel spasm and DCI is weak, and patients can develop infarction in a vascular territory unaffected by arterial constriction. In addition, treatment of angiographic vasospasm does not lead to improved clinical outcomes.

Therefore, it is likely that changes occurring at a cellular level much earlier in the disease process account for much of the damage associated with DCI. A better understanding and measurement of the processes associated with EBI potentially offers a window of opportunity for intervention to prevent further cerebral damage. This is important, as during the first few days following SAH it is currently impossible to predict which patients will subsequently deteriorate.

Significant molecular alterations occur during the EBI phase, including disruption to the NO signalling pathway, which leads to cell apoptosis. Secondary injury such as inflammation, microthrombus formation and generation of reactive oxygen species also lead to cell death. NO depletion plays a key role in these processes. Animal models suggest that after SAH the brain is relatively NO deplete, secondary to endothelial nitric oxide synthase (eNOS) dysfunction and scavenging by haemoglobin.

eNOS generated NO plays a neuroprotective role against the development of brain injury leading to decreases in infarct sizes, thus giving a scientific foundation to therapeutic repletion of NO. After SAH eNOS derived NO has been shown to be a key mediator of neuroprotection. Sodium nitrite (a pro-drug) is particularly suited to restore NO levels in brain injury because it is only converted to NO under conditions of hypoxia or acidosis, targeting the areas that are potentially most at risk. Furthermore one study in human cardiac-arrest survivors has also demonstrated a neuroprotective action.

The safety profile of intravenous sodium nitrite has been well established in humans suffering SAH, demonstrating low toxicity and minimal effects on systemic blood pressure. Cerebral NO donor agents, appear therefore to safely replicate the benefits of eNOS derived NO.

The EEG is sensitive to millisecond changes in brain electrical activity. Quantitative electroencephalography (qEEG) uses power spectral analysis to obtain measures of the different components of the EEG, sensitively detecting disturbed neuronal activity during the development of ischaemia. SAH results in a variety of abnormalities in qEEG parameters all associated with ischaemia. Specifically these are decreases in the alpha/delta ratio (ADR) and a decrease in relative alpha power variability. These patterns have been shown to predict subsequent ischaemia in this patient group with high specificity.

The aim of this study was to use sodium nitrite in combination with qEEG as a physiological probe of neuronal function to investigate the role of NO signalling after severe SAH. We hypothesised the qEEG response to a sodium nitrite infusion (exogenous NO) would be most noticeable in patients with the worst injury as such patients have the greatest capacity for normalising reactions. Such a response would be predicted to consist of restoration of alpha waves and a decrease in the power of slower frequencies such as delta waves, resulting in an increase in the alpha/delta ratio.

Materials and Methods

Subjects

Patients aged 18-80 years admitted to the Neurosciences Intensive Care Unit (NICU) at the John Radcliffe Hospital, Oxford after having suffered severe aneurysmal SAH (WFNS grade 3, 4 or 5 at time of presentation) were eligible for inclusion in the study. There were no specific selection criteria apart from grade of SAH, and the absence of any exclusion criteria (see below). No patient showed clinical or angiographic evidence of delayed ischaemia or vasospasm at the time of the study.

Written informed consent was obtained from the next of kin of all participants, and from participants if they regained capacity to consent. The study was approved by the South Central—Oxford C NHS Health Research Authority Ethics Committee 12/SC/0366.

Exclusion criteria included contraindications to sodium nitrite, specifically severe cardiovascular compromise and pre-existing methaemoglobinaemia. Next of kin provided information regarding smoking, medication, hypertension and family history.

All patients underwent standard clinical care that was not influenced by inclusion in this study. This included therapeutic sedation with a combination of propofol, fentanyl, and midazolam with neuromuscular blockade using atracurium administered as required. CT scans were performed in the event of lack of wakening in sedated patients or worsening of neurological signs in awake patients, as per unit policy. Patients that did not demonstrate neurological deterioration did not undergo scanning in the acute period, however they did later receive follow up MRI imaging at 6 months as per local protocol which confirmed lack of new infarction.

DCI was diagnosed based upon consensus guidelines. In those patients who remained intubated and sedated this was by CT.

Two patients (numbers 2 and 4) had treatment withdrawn and subsequently died after CT evidence of widespread infarction secondary to DCI. The investigators who did the study measured the outcomes but were not responsible for the clinical care of these patients.

Treatment of vasospasm/DCI was via a standardized protocol involving hypertension, maintenance of euvolaemia and maintenance of a haemoglobin >8 g/dL. All patients showing evidence of DCI were treated according to this protocol.

Study Design

Following definitive endovascular aneurysm treatment, each patient underwent a two hour period of continuous EEG monitoring (Porti 7 system, Twente Medical Systems International) on one occasion as soon as was practically possible after endovascular securing of the aneurysm.

An infusion of sodium nitrite at 10 mcg/kg/min was commenced at the start of the second hour of recording, and continued for one hour. The dosing schedule was based upon previous studies using sodium nitrite, and was decided upon to reach a compromise between ensuring adequate delivery of cerebral NO and minimisation of any cardiovascular effects. Sedative drug levels, muscle relaxants and vasopressors were documented and changes in infusion rates were minimised for the duration of the recording.

We used a simplified EEG montage that aimed for compromise between stable maintenance of recording and full coverage of all vascular territories. Consequently, 7-13 unipolar EEG electrodes (depending on the presence of external ventricular drains and intracranial pressure (ICP) monitors) at the following positions defined according to the international 10-20 system: Cz, Fz, Pz, Fp1, Fp2, F3, F4, P3, P4, T3, T4, O1, O2. EEG data were digitized at a sampling rate of 2048 Hz, with a high pass filter of 0.5 Hz and a low pass filter of 30 Hz.

The patients also underwent simultaneous transcranial Doppler (TCD) monitoring. Insonation of the MCA M1 segment was performed unilaterally on the side with the best window using colour-coded duplex ultrasound (EZ-Dop, DWL; 2 Mz probe). One patient (10) did not have an adequate TCD window therefore this was not recorded.

The patient's $PETCO_2$, end-tidal $O_2$, ABP and $SpO_2$ were recorded continuously and collected on a Power-1401 data acquisition interface (Cambridge Electronic Design). All patients had an intracranial pressure monitor inserted, but due to technical issues we were unable to record the ICP waveform for four patients (1, 2, 7 and 13). Arterial $CO_2$ values were collected once during the duration of the recording as part of routine clinical care.

Each surviving patient was followed up at three to six months post-rupture. Telephone follow up was performed for patients who were unable to attend hospital due to their clinical status. Primary outcome was measured by the presence or absence of delayed ischemia. Long term outcome was assessed by modified Rankin scale at 3 months, via structured standardised questions in person or by telephone. The modified Rankin scale, is a commonly used grading system that measures the degree of disability or dependence in the daily activities of people who have suffered a neurological insult. Good outcome is defined as a score of 0-2, whereas poor outcome is defined as ≥3.

Quantitative EEG Analysis

Pre-processing was carried out using custom written MATLAB (MathWorks Inc.) code and the EEGLAB v13.4.3b analysis toolbox. Datasets were re-referenced to the average of bilateral mastoid reference electrodes and band pass filtered from 0.5 to 15 Hz using a linear finite impulse response (FIR) filter. Each EEG recording was visually inspected and artefacts were manually removed. Channels showing evidence of excessive amounts of noise were removed from each recording.

Spectral analysis was carried out using FieldTrip, a MATLAB software toolbox for EEG analysis. Data was windowed into 30-second segments that overlapped by 50%. Time-frequency analysis was performed using a multi-taper spectral estimation using discrete prolate spheroidal (Slepian) sequences with 14 tapers, and fast Fourier transform algorithm for each electrode channel. Five 60-second epochs were selected randomly from the first (baseline) and last thirty minutes of the recording (during infusion). The epochs were separated by at least 60 seconds to avoid autocorrelation. The corresponding frequency distribution in each epoch was identified, which enabled determination of power values in the following frequency bands: delta 1-4 Hz, alpha 8-12 Hz and total low frequency power 1-15 Hz.

Statistical analysis was carried out using R and the analysis package nlme. We applied a two level linear mixed effects multilevel model to the data to allow for within patient correlation due to repeated measures on each patient over time. Age, sedation levels, the presence of delayed ischaemia and the presence of sodium nitrite were included as fixed effects. A qqnorm plot was used to identify any outliers and these were subsequently eliminated from the model. Goodness of fit was assessed via Shapiro-Wilk normality tests on fixed and random effect residuals, and calculation of $R^2$ for the model.

Physiological Data Analysis

Waveform analysis was performed using custom written MATLAB code, enabling calculation of average pre and during infusion values for TCD middle cerebral artery velocity (MCAV) ABP, $PETCO_2$, end-tidal $O_2$ and ICP.

Results

Demographics, Treatment and Outcome 14 patients (mean age 52.8; range 41-69; 11 female) with spontaneous SAH successfully treated with endovascular coiling were recruited over a total study period of 13 months. All patients admitted to the Neurosciences Intensive Care Unit at the John Radcliffe Hospital were eligible for inclusion in the study.

All patients were modified Fisher grade 4 (thick SAH with intra ventricular haemorrhage (IVH)), WFNS grade 3-5 on initial presentation. All patients were intubated and sedated on the NICU. It was necessary to intubate and sedate the WFNS grade 3 patients either due to a subsequent drop in their Glasgow Coma Score (GCS) secondary to seizures or subsequent episodes of vomiting.

Data was collected between 2-4 days (mean 3.5) following primary SAH. Due to cardiovascular instability and unknown behaviour of sodium nitrite in this population at that time it was not possible to collect data sooner than day 4 in patients 2 and 6. Six of the fourteen (43%) of the study patients had a modified Rankin Scale of three or more at three months post-SAH (poor outcome group). Seven (50%) of the study patients developed DCI as defined by the presence of infarction on CT within 6 weeks after SAH that was not present on the CT scan between 24 and 48 hours after aneurysm occlusion, and that was not attributable to other causes such as surgical clipping or endovascular treatment [26]. This is in keeping with a higher incidence of DCI reported in previous studies of high-grade (WFNS grade 3-5) SAH patients.

All patients were diagnosed with hydrocephalus and were treated with external ventricular drainage immediately on admission to the neurosurgical centre. All patients were treated with endovascular embolization.

Three patients died, two from complications following severe delayed cerebral ischaemia and one from cardiovascular instability. Support was withdrawn only after CT diagnosis of widespread infarction. There was no rebleeding. Three patients developed sepsis secondary to chest infection, which were treated with intravenous antibiotics.

qEEG Results

Visual inspection of raw EEG data did not reveal any ictal or pre-ictal activity in any of the recruited patients. Datasets were also examined for evidence of burst suppression. Two outliers were identified which were removed from further analysis.

The results of the two level linear mixed effects model showed the following: Mean baseline ADR in the patients that did not get DCI was 0.033 (SEM=0.008). In these patients, sodium nitrite led to an increase in ADR (mean ADR=0.055, SEM=0.010, p value=<0.000). In those patients who subsequently developed DCI, mean baseline ADR was (mean=0.056, SEM=0.010). In these patients sodium nitrite led to a decrease in ADR (mean ADR=0.0050, SEM=0.009, p value=0.006).

There was evidence of a difference between the baseline ADR in the non-DCI group compared to the DCI group but this did not reach significance (p value=0.0718). These results are illustrated in FIG. 1.

There was no significant effect of age, WFNS grade or propofol levels on the ADR (age mean effect=0.972, SEM=0.1343, p value=0.8344, propofol mean effect=0.0003, SEM=0.0002, p value=0.1158, WFNS mean effect=−0.012, SEM=0.028, p value=0.6856).

A Shapiro-Wilk normality test of the fixed and random effects residuals resulted in p values of 0.5569 and 0.9765 respectively, and the model returned an $R^2$ value of 0.6894.

When looking at the patients with "good outcome" and those with "poor outcome" it was noted that the two groups did not differ significantly in pre-infusion (baseline) relative delta (p=0.93, Mann Witney U, 2 tailed) or relative alpha power (p=0.18, Mann Witney U, 2 tailed).

However, there was a significant decrease in during-infusion relative delta power from a median of 2.88 $uV^2/Hz$ (IQR=2.67-3.00) to a median of 2.63 $uV^2/Hz$ (IQR=2.45-2.80) for the good outcome patients (p=0.02, Wilcoxon matched-pairs rank, 2 tailed). Additionally, there was a significant increase in post infusion relative alpha power (median=0.14 $uV^2/Hz$, IQR=0.09-0.22) compared to baseline (median=0.10 $uV^2/Hz$, IQR=0.07-0.20) (p=0.02, Wilcoxon matched-pairs rank, 2 tailed) and consequently the ADR almost doubled from median=0.03, (IQR=0.03-0.07) to median 0.05 (IQR=0.03-0.08) (p=0.02, Wilcoxon matched-pairs rank, 2 tailed) in the good outcome group. In comparison, there were no significant differences either in the baseline versus during infusion for relative delta power, relative alpha power of ADR for the poor outcome patients. These data are illustrated in FIG. 2.

The percentage change in relative power (i.e. (during infusion−baseline)/baseline)×100) was also calculated to highlight any statistically significant differences between the good and poor outcome groups. The relative alpha power increased by a median of 38.2% (IQR=10.8%-56.8%) for patients with a good outcome and did not change for the patients with a poor outcome, although the trend was negative (median −12.0%, IQR=−17.1%-1.3%). The relative delta power decreased by a median of −7.0% (IQR −9.9%-−4.3%) for the patients with a good outcome and did not change for the patients with a poor outcome (median 0.9%, IQR=−1.1%-13.6%). This resulted in a positive percentage change in the ADR which increased by a median of 50% (IQR=18%-70%) in the good outcome group compared with no change for the poor outcome group (median=−12%, IQR=−32%-2%). These differences were statistically significant—relative alpha power (p=0.003, Mann Witney U, 2 tailed), relative delta power (p=0.005, Mann Witney U, 2 tailed) alpha/delta ratio (p=0.003, Mann Witney U, 2 tailed). These results are illustrated in FIG. 2. FIG. 3 demonstrates the percentage change from baseline ADR over time for the poor outcome and good outcome groups. The baseline ADR in both groups remains constant, indicating that significant changes in the power spectrum secondary to natural fluctuations are unlikely in this time period.

Physiological Data

Arterial blood pressure data was collected on all 14 patients. There was a significant decrease (p=0.026) in the MAP of the patients in response to the sodium nitrite, from a mean MAP of 87 mmHg to 84 mmHg mercury. One patient did not have an adequate transcranial Doppler window for measurement. End tidal $CO_2$ was collected on 13 patients. ICP data was collected on 10 patients. Two patients did not have an intracranial pressure monitor (ICPM) inserted, reflecting current differences in clinical practice in our unit, and technical issues prevented ICP recording from the other two patients.

There were no significant changes in TCD, MCAV, ICP, or end tidal $CO_2$ values as a result of sodium nitrite infusion. The variability in the measurements did not appear to be greatly affected by the sodium nitrite infusion, as the standard deviation for pre and during infusion remained relatively constant.

Discussion

Patients that went on to have a poor outcome showed no significant alpha, delta or alpha/delta ratio response to a 1-hour infusion of sodium nitrite, whereas patients that did have a good outcome showed a significant increase in delta power resulting in an increase in the alpha/delta ratio. Patients that went on to develop DCI showed a significant alpha/delta ratio decrease to a 1-hour infusion of sodium nitrite, whereas patients that did not develop DCI showed a significant increase in the alpha/delta ratio. A decrease in ADR is a qEEG measure that has been associated with the subsequent development of cerebral ischaemia after SAH.

It is important to note that the two groups of patients were indistinguishable at presentation in terms of clinical severity (WFNS score), Fisher grade or baseline qEEG parameters. Therefore the change in qEEG response to sodium nitrite infusion signifies that increasing cerebral NO unmasks cerebral neuronal and metabolic dysfunction that is otherwise not detectable by current clinical methods. The lack of significant change in TCD recordings or ICP suggests that these changes were not due to changes in global cerebral blood flow, but rather were indicative of changes occurring at the neuronal level.

There was a small drop in MAP which was significant statistically but the magnitude of which is very unlikely to have any clinical implications. The lack of change in the TCD in response to the nitrite infusion in particular was as expected, as nitrite is only reduced to NO under conditions of acidosis or hypoxia (secondary to hypoxic nitrite reduction) therefore we would only expect the vascular vasodilatory actions to occur locally and not have measureable effects on the macrovasculature.

These results suggest mechanistic differences in the way the brain responds to increasing cerebral NO, depending on the severity of the injury.

Astrocyte dysfunction and changes in capillary permeability are extremely important in the development of secondary brain injury, with the NO signalling pathway playing a pivotal role in this. One explanation for the lack of EEG response in the poor outcome group and decrease in EEG response in the DCI group is that in these groups there may be greater disruption to the neurovascular signalling cascade that ensures cerebral blood flow is closely matched to neuronal demand. In such a scenario, increased cerebral NO may selectively vasodilate in areas where there is less tissue damage, diverting blood away from the more ischaemic areas in the more severely injured patients. This also implies loss of local autoregulation, which would increase the risk of subsequent infarction.

Another explanation for these results is that the poor outcome patients have a more severe initial brain injury (currently undetectable with the methods available), which results in greater cerebral NO depletion, as demonstrated by several animal models of SAH. It is possible that NO depletion was greater in those who developed DCI and a longer duration of infusion would have demonstrated a move towards a less ischaemic picture (as measured by qEEG). The non DCI patients were not as NO deplete and therefore showed the expected improvement in qEEG parameters during the course of the study.

The importance of the EBI phase as a key window of therapeutic opportunity must also be emphasised. The development of DCI was associated with poor outcome in this study, but this cannot be predicted in the first few days post injury with clinical measures alone. Previous studies using long-term continuous EEG in SAH (an average of 5 days (range 1-60 days)) showed that reduced alpha-delta ratio was strongly associated with the development of DCI in high-grade SAH, compared to a small increase for the patients without DCI. Other long-term studies in moderate and good-grade SAH have shown that a persistent decrease in alpha power from baseline is a consistent marker for DCI. In ischemic stroke it has been demonstrated that slow frequency EEG activity increases as cerebral perfusion falls and the tissues become more ischaemic. There is also loss of higher frequencies such as alpha, resulting in a reduced ADR.

Using a drug in this way enabled the duration of recording to be considerably shorter (approximately 2 hrs) than those used in previous studies which recorded continuously for an average of 5 days (range 1-60 days) before consistent changes were observed. This increases the practicability and usefulness of using qEEG as a marker to enable targeted therapy and prognostication.

By comparing pre-infusion to post infusion values in the same patient each patient acted as their own control, minimising the effects of metabolic alterations, ICP changes or effects of sedation. Sedation levels and physiological parameters were recorded and did not change significantly over the course of the recording for each patient. The level of sedation did not significantly affect the results.

In conclusion, we have shown that a one-hour infusion of intravenous sodium nitrite can induce qEEG changes over a relatively short recording period. Patients that did not subsequently develop DCI and patients that had a good long-term clinical outcome (as defined herein) showed qEEG changes consistent with improved neuronal health, whereas patients that did develop DCI and patients which had a poor long-term clinical outcome (as defined herein) showed changes consistent with the potential development of ischaemia. Therefore this method may represent a potentially useful tool for prognostication in the field of brain injury.

The invention claimed is:

1. A method for assessing the extent of, or risk of developing, delayed cerebral ischemia (DCI) following subarachnoid haemorrhage, said method comprising:

(i) contacting at least a portion of the brain of a subarachnoid haemorrhage subject with a cerebral nitric oxide donor, wherein said nitric oxide donor is a nitrite salt;

(ii) monitoring at least a portion of the brain of the subject with qEEG;

(iii) determining whether or not there is a change in a qEEG parameter indicative of DCI within 360 minutes of said contact between the nitric oxide donor and the brain of the subject; and, (iv) assessing the subject's extent of, or risk of developing, DCI prior to the contact with the nitric oxide donor, wherein an improvement in the qEEG parameter indicative of DCI results in an assessment of a lower extent of DCI or lower risk of developing DCI, as compared to the extent of DCI or the risk of developing DCI in the brain of a subarachnoid haemorrhage subject that was contacted with the cerebral nitric oxide donor, but where the qEEG of that subject did not show an improvement in the qEEG parameter indicative of DCI.

2. The method of claim 1, wherein said monitoring comprises a monitoring step which commences within 360, 300, 240, 180, 120, 90, 75, 60, 45, 30, 15, 5 or 1 minute of, or concurrently with, contacting of the brain with the cerebral nitric oxide donor.

3. The method of claim 2, wherein the results of said monitoring are compared to the results of a monitoring step commenced no more than 360, 300, 240, 180, 120, 90, 75, 60, 45, 30, 15, 5 or 1 minute prior to contacting of the brain with the cerebral nitric oxide donor.

4. The method of claim 1, wherein said monitoring of said subsequent change in said one or more monitoring modality is essentially continuous and commences within 360, 300, 240, 180, 120, 90, 75, 60, 45, 30, 15, 5 or 1 minute before initiation of contact of the brain with the cerebral nitric oxide donor and ceases no more than 24 hrs, 18 hrs, 12 hrs, 10 hrs, 8 hrs, 6 hrs, 5 hrs, 4 hrs, 3 hrs, 2 hrs, 1 hrs or 30 minutes after contact of the brain with an effective amount of the cerebral nitric oxide donor.

5. The method of claim 1, wherein the qEEG parameter is the alpha/delta ratio and/or the relative alpha power variability and/or the relative delta power variability.

6. A method for assessing the extent of, or risk of developing, delayed cerebral ischemia (DCI) following subarachnoid haemorrhage, said method comprising:

(i) contacting at least a portion of the brain of a subarachnoid haemorrhage subject with a cerebral nitric oxide donor, wherein said nitric oxide donor is a nitrite salt;

(ii) monitoring at least a portion of the brain of the subject with qEEG and measuring the alpha/delta ratio;

(iii) determining whether or not there is a change in the alpha/delta ratio within 360 minutes of said contacting between the nitric oxide donor and the brain of the subject; and (iv) assessing the subject's extent of, or risk of developing, DCI prior to the contacting with the nitric oxide donor, wherein an increase in the alpha/delta ratio results in an assessment of a lower extent of DCI or lower risk of developing DCI, as compared to the extent of DCI or the risk of developing DCI in the brain of a subarachnoid haemorrhage subject that was contacted with the cerebral nitric oxide donor, but where the alpha/delta ratio did not change or decreased.

7. The method of claim 6 wherein said nitrite salt is formed from one or more nitrite anions and one or more cations selected from the alkali metals, alkaline earth metals, transition metals, ammonium and organic cations.

8. The method of claim 7 wherein said nitrite salt is selected from lithium nitrite, sodium nitrite, potassium nitrite, magnesium nitrite, and calcium nitrite, preferably sodium nitrite.

9. The method of claim 6, wherein said monitoring and measuring comprises a monitoring and measuring step which commences within 360, 300, 240, 180, 120, 90, 75, 60, 45, 30, 15, 5 or 1 minute of, or concurrently with, contacting of the brain with the cerebral nitric oxide donor.

10. The method of claim 9, wherein the results of said monitoring and measuring are compared to the results of a monitoring and measuring step commenced no more than 360, 300, 240, 180, 120, 90, 75, 60, 45, 30, 15, 5 or 1 minute prior to contact of the brain with the cerebral nitric oxide donor.

11. The method of claim 6, wherein said monitoring and measuring is essentially continuous and commences within 360, 300, 240, 180, 120, 90, 75, 60, 45, 30, 15, 5 or 1 minute before initiation of contact of the brain with the cerebral nitric oxide donor and ceases no more than 24 hrs, 18 hrs, 12 hrs, 10 hrs, 8 hrs, 6 hrs, 5 hrs, 4 hrs, 3 hrs, 2 hrs, 1 hr or 30 minutes after contact of the brain with an effective amount of the cerebral nitric oxide donor.

12. The method of claim 1 wherein said nitrite salt is formed from one or more nitrite anions and one or more cations selected from the alkali metals, alkaline earth metals, transition metals, ammonium and organic cations.

13. The method of claim 12 wherein said nitrite salt is selected from lithium nitrite, sodium nitrite, potassium nitrite, magnesium nitrite, and calcium nitrite, preferably sodium nitrite.

* * * * *